(12) United States Patent
Ozai et al.

(10) Patent No.: US 7,045,572 B2
(45) Date of Patent: *May 16, 2006

(54) ORGANOSILICON COMPOUND

(75) Inventors: Toshiyuki Ozai, Takasaki (JP);
Hiroyasu Hara, Annaka (JP);
Yoshifumi Inoue, Annaka (JP);
Tomoyuki Goto, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/015,024

(22) Filed: Dec. 20, 2004

(65) Prior Publication Data

US 2005/0101791 A1 May 12, 2005

Related U.S. Application Data

(63) Continuation of application No. 09/983,933, filed on Oct. 26, 2001, now Pat. No. 6,849,755.

(30) Foreign Application Priority Data

Oct. 26, 2000 (JP) ............................ 2000-327558

(51) Int. Cl.
*C08G 77/06* (2006.01)
(52) U.S. Cl. ...................... 524/837; 524/588; 525/106; 526/279; 528/32
(58) Field of Classification Search ............... 524/588, 524/837; 525/106; 526/279; 528/32
See application file for complete search history.

(56) References Cited

U.S. PATENT DOCUMENTS

| 4,120,570 A | 10/1978 | Gaylord |
| 4,259,467 A | 3/1981 | Keogh et al. |
| 4,276,402 A | 6/1981 | Chromecek et al. |
| 4,290,869 A | 9/1981 | Pigeon |
| 4,528,081 A | 7/1985 | Lien et al. |
| 4,728,571 A | 3/1988 | Clemens et al. |
| 4,971,831 A | 11/1990 | Ohba et al. |
| 5,158,717 A | 10/1992 | Lai |
| 5,391,677 A | 2/1995 | Arai et al. |
| 5,461,173 A | 10/1995 | Sato et al. |
| 5,856,545 A | 1/1999 | Okawa |
| 6,063,887 A | 5/2000 | Okawa |
| 6,306,999 B1 | 10/2001 | Ozai et al. |
| 6,420,504 B1 | 7/2002 | Yoshitake et al. |
| 6,699,918 B1 | 3/2004 | Ozai et al. |
| 6,849,755 B1 * | 2/2005 | Ozai et al. .................. 556/431 |

FOREIGN PATENT DOCUMENTS

| EP | 0 624 827 | 11/1994 |
| EP | 1 231 241 | 8/2002 |
| JP | 08-281865 | 8/1996 |

OTHER PUBLICATIONS

Yoshida et al (Chem. Abstract 1997:26381; abstract of JP08281865), 1997.
Patent Abstracts of Japan, JP 06-256355, Sep. 13, 1994.

* cited by examiner

*Primary Examiner*—Samuel Barts
(74) *Attorney, Agent, or Firm*—Oblon, Spivak, McClelland, Maier & Neustadt, P.C.

(57) ABSTRACT

An organosilicon compound represented by the following general formula (1):

$$(HC\equiv C-\underset{R^1}{\underset{|}{C}}-\underset{\underset{O}{\|}}{C}-O-Z^1)_{3-m}-Si(R^3)_m-Z^2-Si(R^3)_n(X)_{3-n} \quad (1)$$

wherein $R^1$ is a hydrogen atom, a phenyl group or a halogenated phenyl group; $R^2$ is a hydrogen atom or a methyl group; $R^3$'s are each a substituted or unsubstituted monovalent hydrocarbon group having 1 to 10 carbon atoms; X is a hydrolyzable group; $Z^1$ is —$R^4$—, —$R^4O$— or —$R^4(CH_3)_2SiO$—, where $R^4$ is a substituted or unsubstituted divalent hydrocarbon group having 1 to 10 carbon atoms; $Z^2$ is an oxygen atom or a substituted or unsubstituted divalent hydrocarbon group having 1 to 10 carbon atoms; and m is 0, 1 or 2 and n is 0, 1 or 2. When incorporated in silicone compositions, the organosilicon compound acts as a cross-linking agent having well-balanced photopolymerizability and condensation curability.

6 Claims, No Drawings

ORGANOSILICON COMPOUND

REFERENCE TO PRIOR APPLICATIONS

The present application is a continuation of application Ser. No. 09/983,933, filed on Oct. 26, 2001, now allowed, and in which the entire contents are incorporated herein by reference.

BACKGROUND OF THE INVENTION

1. Field of the Invention

This invention relates to a novel compound, and more particularly to an organosilicon compound having curing mechanisms in two ways in which it cures upon photopolymerization and in which it cures upon absorption of moisture in air, and capable of acting as a cross-linking agent when incorporated in silicone compositions.

2. Description of the Prior Art

A variety of photopolymerizable silicone compounds have already been developed, and these are utilized in ultraviolet radiation-curable adhesives and mold-making agents. Also, adhesives having curing mechanisms in two ways in which they cure by photopolymerization and in which they cure upon absorption of moisture in air (curing of a condensation type) are in wide use at present. However, cross-linking agents used in such compositions having curing mechanisms in two ways make it difficult to balance photopolymerizability with condensation curability, resulting in materials ill-balanced toward either curability.

SUMMARY OF THE INVENTION

Accordingly, an object of the present invention is to provide an organosilicon compound which can well balance photopolymerizability with condensation curability when incorporated in silicone compositions.

As a result of extensive studies made on cross-linking agents, the present inventors have discovered that the photopolymerizability and condensation curability can be made well balanced by incorporating at least two silicon atoms in one molecule to bond a photopolymerizable group and a condensation-curable group individually to different silicon atoms so that these groups can take responsibility of the photopolymerization and the condensation curing, respectively. Thus, they have accomplished the present invention.

More specifically, the present invention provides an organosilicon compound represented by the following general formula (1):

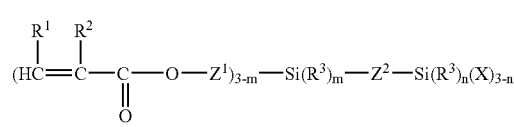

wherein $R^1$ is a hydrogen atom, a phenyl group or a halogenated phenyl group; $R^2$ is a hydrogen atom or a methyl group; $R^3$'s may be the same or different and are each a substituted or unsubstituted monovalent hydrocarbon group having 1 to 10 carbon atoms; X is a hydrolyzable group; $Z^1$ is $-R^4-$, $-R^4O-$ or $-R^4(CH_3)_2SiO-$, where $R^4$ is a substituted or unsubstituted divalent hydrocarbon group having 1 to 10 carbon atoms, and, when the value of 3-m is plural, $R^4$'s may be the same or different; $Z^2$ is an oxygen atom or a substituted or unsubstituted divalent hydrocarbon group having 1 to 10 carbon atoms; and m is 0, 1 or 2 and n is 0, 1 or 2.

DESCRIPTION OF THE PREFERRED EMBODIMENTS

The present invention is described below in detail. The terminology "(meth)acryloyl" herein means acryloyl, methacryloyl, or a combination thereof.

The organosilicon compound of the present invention is a compound represented by the following general formula (1):

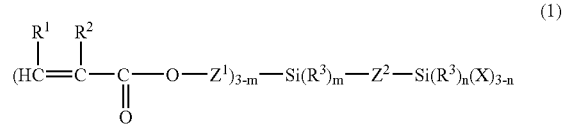

In the formula, $R^1$ is a hydrogen atom, a phenyl group or a halogenated phenyl group. $R^2$ is a hydrogen atom or a methyl group. $R^3$'s may be the same or different and are each a substituted or unsubstituted monovalent hydrocarbon group having 1 to 10 carbon atoms, and preferably 1 to 6 carbon atoms. In the group represented by $R^3$, the substituted monovalent hydrocarbon group may include halogen-substituted monovalent hydrocarbon groups as exemplified by halogenated alkyl groups such as a chloromethyl group, a 2-chloroethyl group, a 2-bromoethyl group, a 1,1-dichloropropyl group, a 3-chloropropyl group and a 3,3,3-trifluoropropyl group. The unsubstituted monovalent hydrocarbon group may include alkyl groups such as a methyl group, an ethyl group, a propyl group, an isopropyl group, a butyl group, an isobutyl group, a tert-butyl group, a pentyl group, a hexyl group, a cyclohexyl group, an octyl group and a decyl group; alkenyl groups such as a vinyl group and an allyl group; aryl groups such as a phenyl group and a tolyl group; and aralkyl groups such as a benzyl group and a phenylethyl group. Alkyl groups and aryl groups are preferred.

X is a hydrolyzable group, which may include, as preferred groups, lower alkoxyl or lower alkenyloxyl groups having 1 to 6 carbon atoms, and particularly 1 to 4 carbon atoms, as exemplified by alkoxyl groups such as a methoxyl group, an ethoxyl group, a propoxyl group, a butoxyl group and a methoxyethoxyl group, and alkenyloxyl groups such as a vinyloxyl group, an allyloxyl group, a propenoxyl group, an isopropenoxyl group and a butenyloxyl group, and may further include acyloxyl groups as exemplified by ketoxime groups such as a dimethylketoxime group and a methylethylketoxime group, or acyloxy groups such as acetoxy groups.

$Z^1$ is a group represented by $-R^4-$, $-R^4O-$ or $-R^4(CH_3)_2SiO-$. $R^4$ is a substituted or unsubstituted divalent hydrocarbon group having 1 to 10 carbon atoms, and preferably 1 to 6 carbon atoms. When the value of 3-m is plural, $R^4$'s may be the same or different. In $R^4$, the substituted divalent hydrocarbon group may include halogen-substituted alkylene groups such as a chloromethylene group, a dichloromethylene group and a chloroethylene group. The unsubstituted divalent hydrocarbon group may include alkylene groups such as a methylene group, an ethylene group, a propylene group and a tetramethylene group, and arylene groups such as a phenylene group.

$Z^2$ is an oxygen atom or a substituted or unsubstituted divalent hydrocarbon group having 1 to 10 carbon atoms, and preferably 1 to 6 carbon atoms. In $Z^2$, the substituted divalent hydrocarbon group may include the same groups exemplified for $R^4$ above, and the unsubstituted divalent hydrocarbon group may include the same groups exemplified for $R^4$ above. Letter symbol m is 0, 1 or 2, and n is 0, 1 or 2.

The organosilicon compound represented by the general formula (1) may include, e.g., organosilicon compounds such as organosilanes, organosilalkylenes, organosilarylenes and organosiloxanes having 2 to 5 silicon atoms in one molecule, which have in one molecule i) 1 to 3 (meth)acryloyloxyl groups and ii) 1 to 3 silicon-bonded hydrolyzable groups such as silicon-bonded alkoxyl groups or silicon-bonded alkenyloxyl groups.

Specific structures of the organosilicon compound represented by the general formula (1) are shown below. Examples are by no means limited to these.

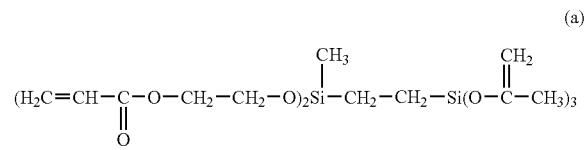
(a)

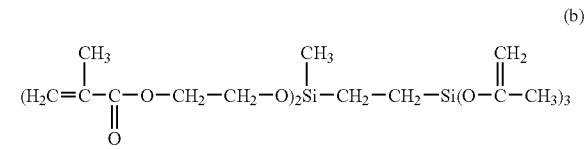
(b)

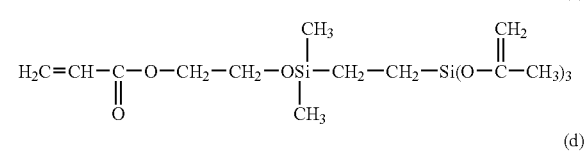
(c)

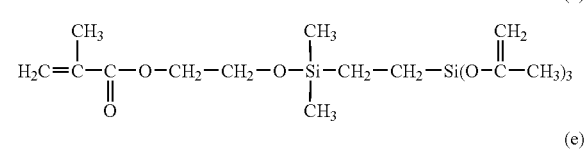
(d)

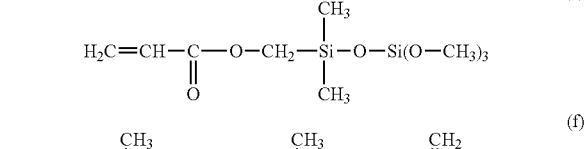
(e)

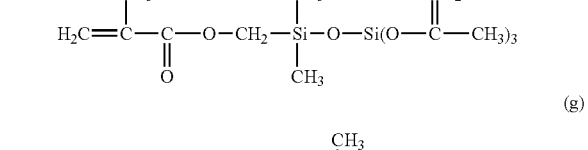
(f)

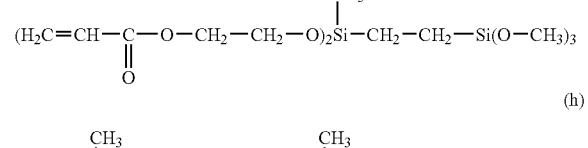
(g)

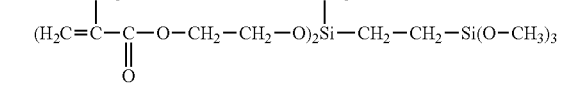
(h)

-continued

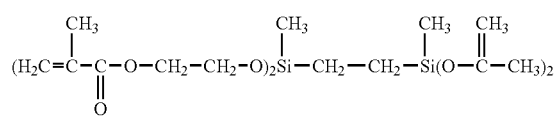
(i)

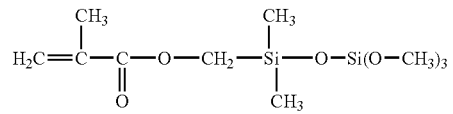
(j)

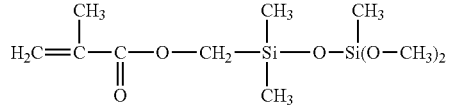
(k)

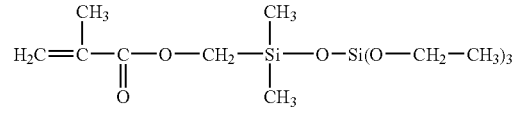
(l)

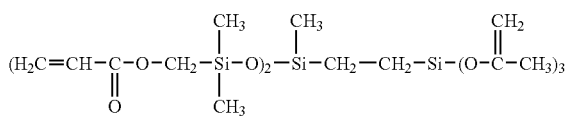
(m)

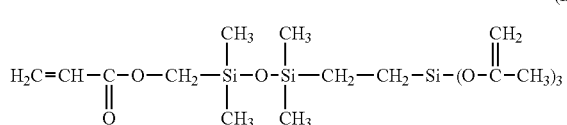
(n)

The organosilicon compound represented by the general formula (1) can be produced, e.g., in the following way.

Firstly, it may be produced by a process represented by the following reaction schemes:

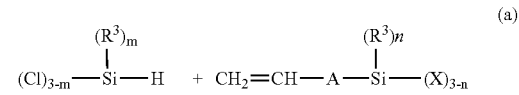
(a)

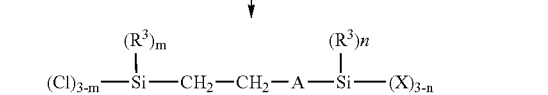

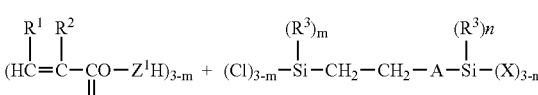
(b)

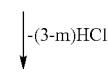

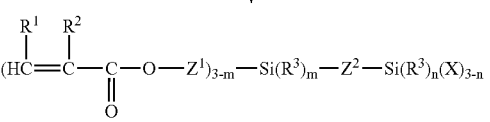

In the above schemes, —$CH_2$—$CH_2$—A— corresponds to —$Z^2$— in the general formula (1), and A is an alkylene group having 1 to 8 carbon atoms, including, e.g., a methylene group, an ethylene group and a propylene group.

Alternatively, it may be produced by a process represented by the following reaction schemes:

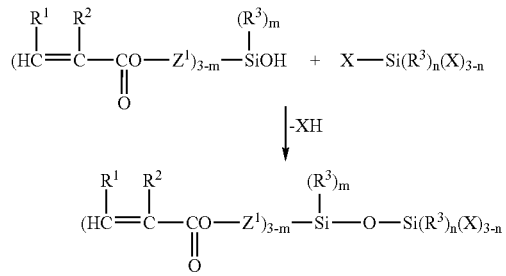

Method of use and purposes:

The organosilicon compound of the present invention has the two properties of photopolymerizability and condensation curability in combination. Hence, it is useful as a cross-linking agent for silicone compositions, and is used in, e.g., adhesives, coating materials and potting materials.

EXAMPLES

The present invention is described below in greater detail by giving Examples. The present invention is by no means limited to these Examples.

Example 1

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added dropwise, and 75.9 g (0.66 mole) of dichloromethylsilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltriisopropenoxysilane reacted completely with the dichloromethylsilane. Its temperature was dropped to about 30° C., and thereafter 133.6 g (1.32 moles) of triethylamine and 0.1 g of butylhydroxytoluene were added to the reaction mixture. Next, 171 g (1.32 moles) of hydroxyethyl methacrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 238.1 g of 1-methylbis(2-methacryloxyethoxy)silyl-2-triisopropenoxysilylethane [the compound of formula (b); yield: 80%).

The above compound was identified by NMR and IR.
NMR: (0.105 ppm, S, 3H, Si—$CH_3$) (0.65~0.79 ppm, broad, 4H, —$CH_2$—$CH_2$—) (1.79 ppm, S, 9H, O—C—$CH_3$) (1.90 ppm, S, 6H, =C—$CH_3$) (3.86~4.10 ppm, broad, 8H, —O—$CH_2$—$CH_2$—O—) (4.10, 4.26 ppm, d, 6H, O—C=$CH_2$) (5.52, 6.08 ppm, d, 4H, $CH_2$=C)
IR: (2,800~3,000 $cm^{-1}$, $^\nu$CH) (1,650 $cm^{-1}$, $^\nu$C=C) (1,700 $cm^{-1}$, $^\nu$C=O) (1,150 $cm^{-1}$, $^\nu$Si—OC)

Example 2

In a 1-liter four-necked flask having a coiled condenser and a thermometer, 88.8 g (0.6 mole) of vinyltrimethoxysilane and 200 g of toluene were added, and then heated to 40° C. After the heating, 0.1 g of a 2% chloroplatinic acid solution in 2-ethylhexanol was added, and 75.9 g (0.66 mole) of dichloromethylsilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltrimethoxysilane reacted completely with the dichloromethylsilane. Its temperature was dropped to about 30° C., and thereafter 133.6 g (1.32 moles) of triethylamine and 0.1 g of butylhydroxytoluene were added to the reaction mixture. Next, 171 g (1.32 moles) of hydroxyethyl methacrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 221 g of 1-methylbis(2-methacryloxyethoxy)silyl-2-trimethoxysilylethane [the compound of formula (h); yield: 84%).

The above compound was identified by NMR and IR.
NMR: (0.105 ppm, S, 3H, Si—$CH_3$) (0.65~0.79 ppm, broad, 4H, —$CH_2$—$CH_2$—) (1.90 ppm, S, 6H, =C—$CH_3$) (3.86~4.10 ppm, broad, 8H, —O—$CH_2$—$CH_2$—O—) (3.3 ppm, S, 9H, O—$CH_3$) (5.52, 6.08 ppm, d, 4H, $CH_2$=C)
IR: (2,800~3,000 $cm^{-1}$, $^\nu$CH) (1,650 $cm^{-1}$, $^\nu$C=C) (1,700 $cm^{-1}$, $^\nu$C=O) (1,150 $cm^{-1}$, $^\nu$Si—OC)

Example 3

In a 1-liter four-necked flask having a coiled condenser and a thermometer, 88.8 g (0.6 mole) of vinyltrimethoxysilane and 200 g of toluene were added, and then heated to 40° C. After the heating, 0.1 g of a 2% chloroplatinic acid solution in 2-ethylhexanol was added, and 75.9 g (0.66 mole) of dichloromethylsilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltrimethoxysilane reacted completely with the dichloromethylsilane. Its temperature was dropped to about 30° C., and thereafter 133.6 g (1.32 moles) of triethylamine and 0.1 g of butylhydroxytoluene were added to the reaction mixture. Next, 153 g (1.32 moles) of hydroxyethyl acrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 209 g of 1-methylbis(2-acryloxyethoxy)silyl-2-trimethoxysilylethane [the compound of formula (g); yield: 84%).

The above compound was identified by NMR and IR.
NMR: (0.105 ppm, S, 3H, Si—$CH_3$) (0.65~0.79 ppm, broad, 4H, —$CH_2$—$CH_2$—) (1.90 ppm, t, 2H, C=CH) (3.86~4.10 ppm, broad, 8H, —O—$CH_2$—$CH_2$—O—) (3.3 ppm, S, 9H, O—$CH_3$) (5.52, 6.08 ppm, d, 4H, $CH_2$=C)
IR: (2,800~3,000 $cm^{-1}$, $^\nu$CH) (1,650 $cm^{-1}$, $^\nu$C=C) (1,700 $cm^{-1}$, $^\nu$C=O) (1,150 $cm^{-1}$, $^\nu$Si—OC)

Example 4

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added, and 61.7 g (0.66 mole) of dimethylchlorolsilane was added. After the addition was completed, the reaction was carried out at 60 to 70° C. for 1 hour while unreacted dimethylchlorolsilane was refluxed, and further at 80 to 90° C. for 2 hours. After the reaction was completed, using gas chromatography, it was confirmed that the vinyltriisopropenoxysilane reacted completely with the dimethylchlorolsilane. Its temperature was dropped to about 30° C., and thereafter 133.6 g (1.32 moles) of triethylamine and 0.1 g of butylhydroxytoluene were added to the reaction mixture. Next, 85.4 g (0.66 mole) of hydroxyethyl methacrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 206 g of 1-dimethyl(2-methacryloxyethoxy)silyl-2-triisopropenoxysilylethane [the compound of formula (d); yield: 80%).

The above compound was identified by NMR and IR.

NMR: (0.105 ppm, S, 6H, Si—CH$_3$) (0.65~0.79 ppm, broad, 4H, —CH$_2$—CH$_2$—) (1.80 ppm, S, 3H, C—CH$_3$) (1.90 ppm, S, 9H, =C—CH$_3$) (3.86~4.10 ppm, broad, 4H, —O—CH$_2$—CH$_2$—O—) (4.0, 4.25 ppm, d, 6H, O—C=CH$_2$) (5.45, 6.1 ppm, d, 2H,CH$_2$=C)

IR: (2,800~3,000 cm$^{-1}$, $^v$CH) (1,650 cm$^{-1}$, $^v$C=C) (1,700 cm$^{-1}$, $^v$C=O) (1,150 cm$^{-1}$, $^v$Si—OC)

Example 5

In a 1-liter four-necked flask having a coiled condenser and a thermometer, 152 g (1.0 mole) of tetramethoxysilane and 1 g of tin dioctate were added, and then heated to 80° C. Thereafter, 160 g (1.0 mole) of acryloxymethyldimethylsilanol was dropwise added. After the addition was completed, the resultant mixture was aged at 80° C. for 2 hours. After the aging, the mixture was distilled under reduced pressure at 92° C./399 Pa (3 mmHg) to obtain 182 g of acryloxymethyldimethylsiloxytrimethoxysilane [the compound of formula (e); yield: 65%).

The above compound was identified by NMR and IR.

NMR: (0.105 ppm, S, 6H, Si—CH$_3$) (3.3 ppm, S, 9H, O—CH$_3$) (3.63 ppm, S, 2H, Si—CH$_2$—) (5.58~6.35 ppm, broad, 3H, CH$_2$=CH—)

IR: (2,800~3,000 cm$^{-1}$, $^v$CH) (1,650 cm$^{-1}$, $^v$C=C) (1,700 cm$^{-1}$, $^v$C=O) (1,150 cm$^{-1}$, $^v$Si—OC)

Example 6

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added, and 75.9 g (0.66 mole) of dichloromethylsilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltriisopropenoxysilane reacted completely with the dichloromethylsilane. Its temperature was dropped to about 30° C., and thereafter 133.6 g (1.32 moles) of triethylamine and 0.1 g of butylhydroxytoluene were added to the reaction mixture. Next, 211 g (1.32 moles) of acryloxymethyldimethylsialnol was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 225 g of 1-methylbis(acryloxymethyldimethylsiloxy)silyl-2-triisoprope noxysilylethane [the compound of formula (m); yield: 80%).

The above compound was identified by NMR and IR.

NMR: (0.105 ppm, S, 15H, Si—CH$_3$) (0.65~0.79 ppm, broad, 4H, —CH$_2$—CH$_2$—) (1.90 ppm, S, 9H, =C—CH$_3$) (3.63 ppm, S, 4H, Si—CH$_2$—) (4.10, 4.26 ppm, d, 6H, O—C=CH$_2$) (5.58~6.35 ppm, broad, 3H, CH$_2$=CH—)

IR: (2,800~3,000 cm$^{-1}$, $^v$CH) (1,650 cm$^{-1}$, $^v$C=C) (1,700 cm$^{-1}$, $^v$C=O) (1,150 cm$^{-1}$, $^v$Si—OC)

Example 7

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added, and 61.7 g (0.66 mole) of dichloromethylsilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltriisopropenoxysilane reacted completely with the dichloromethylsilane. Its temperature was dropped to about 30° C., and thereafter 66.8 g (0.66 mole) of triethylamine and 0.1 g of butylhydroxytoluene were added to the reaction mixture. Next, 105.5 g (0.66 mole) of acryloxymethyldimethylsialnol was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 213 g of 1-dimethyl(acryloxymethyldimethylsiloxy)silyl-2-triisopropenoxysilylethane [the compound of formula (n); yield: 80%).

The above compound was identified by NMR and IR.

NMR: (0.105 ppm, S, 12H, Si—CH$_3$) (0.65~0.79 ppm, broad, 4H, —CH$_2$—CH$_2$—) (1.90 ppm, S, 9H, =C—CH$_3$) (3.63 ppm, S, 2H, Si—CH$_2$—) (4.10, 4.26 ppm, d, 6H, O—C=CH$_2$) (5.58~6.35 ppm, broad, 3H, CH$_2$=CH—)

IR: (2,800~3,000 cm$^{-1}$, $^v$CH) (1,650 cm$^{-1}$, $^v$C=C) (1,700 cm$^{-1}$, $^v$C=O) (1,150 cm$^{-1}$, $^v$Si—OC)

Example 8

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added, and 75.9 g (0.66 mole) of dichloromethyisilane was added. After the addition was completed, the reaction was carried out at 60 to 70° C. for 1 hour while unreacted dichloromethylsilane was refluxed, and further at 80 to 90° C. for 2 hours. After the reaction was completed, using gas chromatography, it was confirmed that the vinyltriisopropenoxysilane reacted completely with the dichloromethylsilane. Its temperature was dropped to about 30° C., and thereafter 133.6 g (1.32 moles) of triethylamine and 0.1 g of butylhydroxytoluene were added to the reaction mixture. Next, 153 g (1.32 moles) of hydroxyethyl acrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 227 g of 1-methylbis(2-acryloxyethoxy)silyl-2-triisopropenoxysilylethane [the compound of formula (a); yield: 80%].

The above compound was identified by NMR and IR.
NMR: (0.105 ppm, S, 3H, Si—$CH_3$) (0.65~0.79 ppm, broad, 4H, —$CH_2$—$CH_2$—) (1.90 ppm, S, 9H, =C—$CH_3$) (3.86~4.10 ppm, broad, 8H, —O—$CH_2$—$CH_2$—O—) (4.10, 4.26 ppm, d, 6H, O—C=$CH_2$) (5.58~6.35 ppm, broad, 6H, $CH_2$=CH—)
IR: (2,800~3,000 $cm^{-1}$, $^\nu$CH) (1,650 $cm^{-1}$, $^\nu$C=C) (1,700 $cm^{-1}$, $^\nu$C=O) (1,150 $cm^{-1}$, $^\nu$Si—OC)

Example 9

In a 1-liter four-necked flask having a coiled condenser and a thermometer, 135.6 g (0.6 mole) of vinyltriisopropenoxysilane and 200 g of toluene were added, and then heated to 40° C. After the heating, 0.1 g of a 2% chloroplatinic acid solution in 2-ethylhexanol was added, and 61.7 g (0.66 mole) of dimethylchlorolsilane was added. After the addition was completed, the reaction was carried out at 60 to 70° C. for 1 hour while unreacted dimethylchlorolsilane was refluxed, and further at 80 to 90° C. for 2 hours. After the reaction was completed, using gas chromatography, it was confirmed that the vinyltriisopropenoxysilane reacted completely with the dimethylchlorolsilane. Its temperature was dropped to about 30° C., and thereafter 66.8 g (0.66 mole) of triethylamine and 0.1 g of butylhydroxytoluene were added to the reaction mixture. Next, 76.5 g (0.66 mole) of hydroxyethyl acrylate was dropwise added. After the addition was completed, the resultant mixture was aged at 60° C. for 3 hours, and the triethylamine hydrochloride precipitated was filtered off. After the filtration, the unreacted components were removed by concentration at 60 to 70° C./665 Pa (5 mmHg) for 2 hours to obtain 206 g of 1-dimethyl(2-acryloxyethoxy)silyl-2-triisopropenoxysilylethane [the compound of formula (c); yield: 80%].

The above compound was identified by NMR and IR.
NMR: (0.105 ppm, S, 6H, Si—$CH_3$) (0.65·0.79 ppm, broad, 4H, —$CH_2$—$CH_2$—) (1.90 ppm, S, 9H, =C—$CH_3$) (3.86~4.10 ppm, broad, 4H, —O—$CH_2$—$CH_2$—O—) (4.10, 4.26 ppm, d, 6H, O—C=$CH_2$) (5.58~6.35 ppm, broad, 3H, $CH_2$=CH—)
IR: (2,800~3,000 $cm^{-1}$, $^\nu$CH) (1,650 cm hu -1, $^\nu$C=C) (1,700 $cm^{-1}$, $^\nu$C=O) (1,150 $cm^{-1}$, $^\nu$Si—OC)

Application Example

An application example is given below in which the organosilicon compound of the present invention is used as a cross-linking agent of a silicone composition.

Into a 3-liter Shinagawa mixing stirrer, 1,000 g of α,ω-hydroxypolydimethylsiloxane having a molecular weight of 20,000, 100 g of 1-methylbis(2-methacryloxyethoxy)silyl-2-triisopropenoxysilylethane as a cross-linking agent, 5 g of tetramethylguanidylpropyltrimethoxysilane as a condensation catalyst and 20 g of diethoxyacetophenone as a UV-curing catalyst were charged, and were deaerated and mixed for 20 minutes. After the deaeration, a UV/condensation double-curing composition was obtained. In the following, general properties of cured products obtained in a case in which the composition was cured by condensation, a case in which it was cured by UV radiation, and a case in which it was cured by the combination of UV radiation+condensation.

Measurement of Physical Properties:
Viscosity:
Measured in accordance with JIS K 6249.
Tack-free time:
A composition is exposed to an atmosphere in the conditions of 23° C. and 55% RH. The time taken until the surface of the composition get dry to the touch, is measured.
Mechanical properties of cured products:
Measured in accordance with JIS K 6301.
Electric properties of cured products:
Measured in accordance with JIS K 6249.

(1) Physical properties of the composition before curing:

TABLE 1

| External appearance | Pale-yellow and semitransparent |
|---|---|
| Viscosity (25° C.) | 2 Pa · s |
| Tack-free time (minute) | 8 |

(2) Physical properties after curing:

TABLE 2

Condensation Curing[1]

| External appearance after curing | Pale-yellow and semitransparent |
|---|---|
| Hardness (durometer, type A) | 27 |
| Elongation | 60(%) |
| Tensile strength | 0.4(MPa) |
| Tensile-shear bond strength (glass) | 0.1(MPa) |
| Specific gravity after curing | 1.01 |
| Volume resistivity | 21(TΩ · m) |
| Dielectric constant (50 Hz) | 2.2 |
| Dielectric dissipation factor (50 Hz) | 0.0022 |

[1]Remarks: Curing conditions: The composition was left at 23° C./55% RH for 7 days.

TABLE 3

UV-radiation Curing[2]

| External appearance after curing | Pale-yellow and semitransparent |
|---|---|
| Hardness (durometer, type A) | 24 |
| Elongation | 20(%) |
| Tensile strength | 0.1(MPa) |
| Tensile-shear bond strength (glass) | 0.1(MPa) |
| Specific gravity after curing | 1.01 |
| Cure depth | 3.8(mm) |
| Volume resistivity | 0.8(TΩ · m) |
| Dielectric constant (50 Hz) | 2.55 |
| Dielectric dissipation factor (50 Hz) | 0.0057 |

[2]Remarks: Curing conditions: The composition was exposed for 5 seconds to a light from a high-pressure mercury lamp (80 W/cm) 10 cm distant from the composition, This irradiation was carried out three times.

TABLE 4

Curing by UV Radiation[3] + Condensation

| External appearance after curing | Pale-yellow and semitransparent |
|---|---|
| Hardness (durometer, type A) | 26 |

TABLE 4-continued

| Curing by UV Radiation[3] + Condensation | |
| --- | --- |
| Elongation | 50(%) |
| Tensile strength | 0.4(MPa) |
| Tensile-shear bond strength (glass) | 0.11(MPa) |
| Specific gravity after curing | 1.01 |
| Volume resistivity | 5.0(TΩ · m) |
| Dielectric constant (50 Hz) | 2.5 |
| Dielectric dissipation factor (50 Hz) | 0.0097 |

[3]Remarks: Curing conditions: The composition was exposed for 5 seconds to a light from a high-pressure mercury lamp (80 W/cm) 10 cm distant from the composition. This irradiation was carried out three times.

The composition was applied on a part of the respective adherends of materials shown in Table 5 below, and then cured under the respective curing conditions. Thereafter, the resulting piece of cured-film was clawed with nails at their edge and at the interface between the cured film and the adherend to examine their adherence.

The results are shown below.

TABLE 5

| | Adherence | | |
| --- | --- | --- | --- |
| | Curing type | | |
| Adherends | UV Radiation curing | UV Radiation + Condensation curing | Condensation curing |
| Aluminum | ○ | ○ | ○ |
| Copper | ○ | ○ | ○ |
| Glass | ○ | ○ | ○ |
| Epoxy resin | ○ | ○ | ○ |
| Polycarbonate | ○ | ○ | ○ |
| Acrylic resin | ○ | ○ | Δ |
| PBT | ○ | ○ | Δ |

"○": Good adhesion (i.e., No peeling occurred)
"Δ": A little poor adhesion (i.e., Slight peeling occurred)

As described above, the organosilicon compound of the present invention provides curing mechanisms in two ways for polymer compositions in which it cures a composition based upon photopolymerization and in which it cures the composition by absorption of moisture in air. Hence, when incorporated in silicone compositions, it acts as a cross-linking agent having well-balanced photopolymerizability and condensation curability.

What is claimed is:

1. A method comprising cross-linking a silicone composition with an organosilicon compound, represented by the following general formula (1):

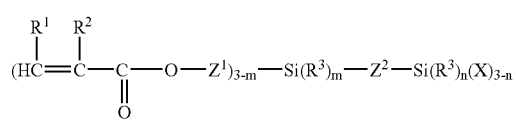

wherein $R^1$ is a hydrogen atom, a phenyl group or a halogenated phenyl group; $R^2$ is a hydrogen atom or a methyl group; $R^3$'s may be the same or different, and are each a substituted or unsubstituted monovalent hydrocarbon group having 1 to 10 carbon atoms; X is a hydrolyzable group; $Z^1$ is $-R^4-$, $-R^4O-$ or $-R^4(CH_3)_2SiO-$, where $R^4$ is a substituted or unsubstituted divalent hydrocarbon group having 1 to 10 carbon atoms, and, when the value of "3-m" is plural, $R^4$'s may be the same or different; $Z^2$ is a substituted or unsubstituted divalent hydrocarbon group having 1 to 10 carbon atoms; and m is 0, 1 or 2 and n is 0, 1 or 2.

2. A method comprising cross-linking a silicone composition with an organosilicon compound, represented by the following general formula (1):

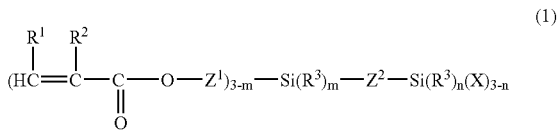

wherein $R^1$ is a hydrogen atom, a phenyl group or a halogenated phenyl group; $R^2$ is a hydrogen atom or a methyl group; $R^3$'s may be the same or different, and are each a substituted or unsubstituted monovalent hydrocarbon group having 1 to 10 carbon atoms; X is a hydrolyzable group; $Z^1$ is $R^4-$, $-R^4O-$ or $-R^4(CH_3)_2SiO-$, where $R^4$ is a methylene group; $Z^2$ is an oxygen atom; and m is 0, 1 or 2 and n is 0, 1or 2.

3. The method of claim 1, wherein $R^1$ is a hydrogen atom, a phenyl group or a halogenated phenyl group; $R^3$ is selected from the group consisting of halogenated alkyl groups, alkyl groups, alkenyl groups, aryl groups, and aralkyl groups; X is selected from the group consisting of alkoxyl groups, alkenyloxy groups, ketoxime groups, and acyloxy groups; $R^4$ is selected from the group consisting of halogen-substituted alkylene groups, alkylene groups, and arylene groups; and $Z^2$ is selected from the group consisting of halogen-substituted alkylene groups, alkylene groups, and arylene groups.

4. The method of claim 2, wherein $R^1$ is a hydrogen atom, a phenyl group or a halogenated phenyl group; $R^3$ is selected from the group consisting of halogenated alkyl groups, alkyl groups, alkenyl groups, aryl groups, and aralkyl groups; and X is selected from the group consisting of alkoxyl groups, alkenyloxy groups, ketoxime groups, and acyloxy groups.

5. A method comprising cross-linking a silicone composition with an organosilicon compound, represented by the following general formula (1):

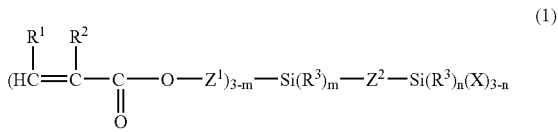

wherein $R^1$ is a hydrogen atom, a phenyl group or a halogenated phenyl group; $R^2$ is a hydrogen atom or a methyl group; $R^3$'s may be the same or different, and are each a substituted or unsubstituted monovalent hydrocarbon group having 1 to 10 carbon atoms; X is a hydrolyzable group; $Z^1$ is $-R^4-$, $-R^4O-$ or $-R^4(CH_3)_2SiO-$, where $R^4$ is a substituted or unsubstituted divalent hydrocarbon group having 1 to 10 carbon atoms, and, when the value of "3-m" is plural, $R^4$'s may be the same or different; $Z^2$ is an oxygen atom or a substituted or unsubstituted divalent hydrocarbon group having 1 to 10 carbon atoms; and m is 0, 1 or 2 and n is 0, 1 or 2.

6. The method of claim 5, wherein $R^1$ is a hydrogen atom, a phenyl group or a halogenated phenyl group; $R^3$ is selected from the group consisting of halogenated alkyl groups, alkyl groups, alkenyl groups, aryl groups, and aralkyl groups; X is selected from the group consisting of alkoxyl groups, alkenyloxy groups, ketoxime groups, and acyloxy groups; $R^4$ is selected from the group consisting of halogen-substituted alkylene groups, alkylene groups, and arylene groups; and $Z^2$ is selected from the group consisting of an oxygen atom, halogen-substituted alkylene groups, alkylene groups, and arylene groups.

* * * * *